(12) United States Patent
Håkansson et al.

(10) Patent No.: US 11,134,924 B2
(45) Date of Patent: Oct. 5, 2021

(54) BIOLOGICAL SAMPLE COLLECTING DEVICE

(71) Applicant: Vilkah Aps, Hedehusene (DK)

(72) Inventors: Kåre Håkansson, Copenhagen V (DK); Per Rosenberg Jensen, Holmegaard (DK); Bjarne Andersen, Frederikssund (DK); Karsten Videbæk, Jyllinge (DK)

(73) Assignee: Vilkah ApS, Hedehusene (DK)

( * ) Notice: Subject to any disclaimer, the term of this patent is extended or adjusted under 35 U.S.C. 154(b) by 588 days.

(21) Appl. No.: 16/072,935

(22) PCT Filed: Jan. 27, 2017

(86) PCT No.: PCT/DK2017/050019
§ 371 (c)(1),
(2) Date: Jul. 26, 2018

(87) PCT Pub. No.: WO2017/129197
PCT Pub. Date: Aug. 3, 2017

(65) Prior Publication Data
US 2019/0029653 A1    Jan. 31, 2019

(30) Foreign Application Priority Data
Jan. 28, 2016 (DK) .......................... PA 2016 70043

(51) Int. Cl.
*A61B 10/00* (2006.01)
*A61B 10/04* (2006.01)
*A61F 13/38* (2006.01)

(52) U.S. Cl.
CPC .......... *A61B 10/0045* (2013.01); *A61B 10/04* (2013.01); *A61F 13/38* (2013.01); *A61B 10/0096* (2013.01); *A61B 2010/0054* (2013.01)

(58) Field of Classification Search
None
See application file for complete search history.

(56) References Cited

U.S. PATENT DOCUMENTS

| 4,023,559 A | 5/1977 | Gaskell |
| 4,157,709 A | 6/1979 | Schuster et al. |

(Continued)

FOREIGN PATENT DOCUMENTS

| EP | 0479619 A1 | 4/1992 |
| GB | 2511551 A | 9/2014 |

(Continued)

OTHER PUBLICATIONS

Int'l Preliminary Report on Patentability dated Mar. 28, 2018 in Int'l Application No. PCT/DK2017/050019.

*Primary Examiner* — Kaylee R Wilson
*Assistant Examiner* — Jay B Shah
(74) *Attorney, Agent, or Firm* — Ice Miller LLP

(57) ABSTRACT

A sample collecting device for collecting samples of cellular material includes an outer tubular member, an inner tubular member and a swab having a tip. At least one guiding element supports and slidably arranges the swab in the inner tubular member such that there is a free space around the swabbing tip. A flexible valve is arranged at a distal end of the outer tubular member. In a storage configuration, the valve is closed and seals the distal end of the outer tubular member. In a sampling configuration, the valve is open such that the swab is slidable to extend through the distal end of the outer tubular member without contacting the valve. A swab kit for collecting and storing samples of cellular material from body cavities includes a sample collecting device and a sealable container adapted to receive and store at least a part of the sample collecting device.

20 Claims, 4 Drawing Sheets

(56) References Cited

U.S. PATENT DOCUMENTS

| | | | |
|---|---|---|---|
| 4,318,414 A | | 3/1982 | Schuster et al. |
| 4,586,604 A | | 5/1986 | Alter |
| 5,129,402 A | * | 7/1992 | Koll ................... A61B 10/0291 |
| | | | 600/572 |
| 5,339,828 A | | 8/1994 | Keating et al. |
| 2005/0137448 A1 | | 6/2005 | Iningler et al. |
| 2014/0330167 A1 | | 11/2014 | Speck et al. |
| 2015/0224497 A1 | * | 8/2015 | Furrer ................ B01L 3/50825 |
| | | | 422/509 |

FOREIGN PATENT DOCUMENTS

| | | |
|---|---|---|
| WO | 83/01741 A1 | 5/1983 |
| WO | 97/32517 A1 | 9/1997 |
| WO | 2014/135899 A1 | 9/2014 |

\* cited by examiner

BIOLOGICAL SAMPLE COLLECTING DEVICE

CROSS-REFERENCE TO RELATED APPLICATION

This application is a Section 371 of International Application No. PCT/DK2017/050019, filed Jan. 27, 2017, which was published in the English language on Aug. 3, 2017, under International Publication No. WO 2017/129197 A1, which claims priority under 35 U.S.C. § 119(b) to Danish Application No. PA 2016 70043, filed Jan. 28, 2016, the disclosures of each of which are incorporated herein by reference.

The present disclosure relates to a sample collecting device for collecting samples of cellular material from body cavities. More particularly, it relates to an improved microbiological swab or bacterial swab. The disclosure further relates to a swab kit comprising the microbiological/bacterial swab.

BACKGROUND OF INVENTION

A swab is a stick with one or both ends coated with an absorbent padding, usually made of cotton. Typically the swab comprises a stick or shaft of plastic and a swabbing tip made of fibrous material such as cotton fibers, wool, polyester fibers or rayon fibers. The cotton swab was originally developed for cleaning the ear. More recent use of swabs includes collecting samples with the purpose of e.g. detecting the presence of microorganisms.

Swabs for collecting samples are often used in narrow spaces, such as the nose, throat, ears or areas in the mouth. When the swab is introduced in these spaces, there may be a risk of contamination of the swabbing tip or stick during insertion and/or retraction of the swab. As an example, humans have nasal hairs in the anterior nasal passage. Sinusitis (or rhinosinusitis) is an inflammation of the mucous membrane that lines the paranasal sinuses. Sinusitis can be due to e.g. bacterial or viral infection. Antibiotics may be used as treatment in some cases, but are not recommended in other cases. *Staphylococcus aureus* is a bacterium that is frequently found in the anterior nasal passage and/or nasal vestibule.

When the swab is introduced (or retracted) through the anterior nasal passage for collecting samples at e.g. the nasal mucous membrane, the swabbing tip and/or stick are directly exposed to material and substances located in the passage and may thus be contaminated with e.g. *Staphylococcus aureus* that colonize the nasal vestibule. Culture directed antibiotic prescription is commonly used, but if the swab is contaminated during insertion/retraction, the antibiotics could be directed against the wrong pathogen or wrongly prescribed when antibiotics are not needed.

SUMMARY OF INVENTION

The present disclosure relates to a sample collecting device for collecting samples of cellular material from body cavities, more particularly in cavities reached by insertion through narrow passages, such as nose, throat and ears. In one embodiment, the sample collecting device is a nose swabbing sampling device. By maintaining a free space around the swabbing tip of a swab, contamination of the swabbing tip is prevented.

In a first embodiment, the presently disclosed sample collecting device for collecting samples of cellular material from body cavities comprises:
- an outer tubular member;
- an inner tubular member slidably arranged inside the outer tubular member;
- a swab comprising a stick; and a swabbing tip;
- one or more guiding elements configured to support and slidably arrange the swab in the inner tubular member such that there is a free space around the swabbing tip; and
- a flexible valve arranged at a distal end of the outer tubular member, the device configured such that:
  - in a storage configuration, the valve is closed and seals the distal end of the outer tubular member, and
  - in a sampling configuration, the valve is open in a position such that the swab can be slid in a longitudinal direction of the device to extend through the distal end of the outer tubular member without the swab being in contact with the valve.

The design of the sample collection device prevents that the swab is contaminated during insertion or retraction through a narrow passage. In the storage configuration, which is typically used during insertion and retraction, the swabbing tip is protected since the valve is closed and the outer tubular member thereby sealed in the distal end, which is the end that enters the passage first. When the swabbing tip is to collect a sample, the swab is slid in a longitudinal direction of the device towards the distal end to extend through the distal end without touching the valve, which is open in the sampling configuration. Preferably, in an intermediate step between the storage configuration and the sampling configuration, the inner tubular member is slid in a longitudinal direction of the device towards the distal end to extend through the distal end, thereby opening the valve and maintaining it open. Once the inner tubular member has opened the valve, the swab may be slid to extend through the distal end without touching the valve as described. The device may thereby be seen as a telescopic device being collapsed in the storage configuration and extended in the sampling configuration. When the sample has been collected, the telescopic device is preferably retracted by, in a first step, retracting the swab to a position inside the tubular member such that it does not extend beyond the distal end of the inner tubular member, and, in a second step, retracting the inner tubular member such that it does not extend beyond the distal end of the outer tubular member. The device may in this regard be arranged such that the valve is maintained open by the inner tubular member in the first step, and such that the valve closes during the second step.

In order to maintain a free space around the swabbing tip, the device comprises guiding elements configured to support and slidably arrange the swab in the inner tubular member. The guiding elements are preferably located inside the inner tubular member and may be e.g. annular extensions on the stick. In such a configuration, a space between the swabbing tip and the inner tubular member is maintained. When the device has been inserted through a narrow passage using the storage configuration, the inner tubular member can be pushed in the distal direction to open the valve while the swab stays inside the inner tubular member. When the valve has been opened by the inner tubular member, the swab can be pushed in the distal direction to extend beyond the valve, without touching the valve, which may have been contaminated during insertion. Similarly, when the device is to be retracted after collecting the samples, the swab is preferably pulled into the inner tubular member in a first step, and the inner tubular member pulled into the outer tubular member in a second step. After the second step, the device is configured in the storage configuration, and can be retraced from the area where samples have been collected, e.g. the nasal mucous membrane.

The sample collecting device may further comprise a light channel and optionally a light source. In one embodiment the outer tubular member further comprises a light channel extending along or inside the outer tubular member. The light channel may be for example an optical fiber. A light source may be added as a separate component or be integrated in the sample collecting device. Such a light source is preferably arranged such that it emits light through the light channel.

The disclosure further relates to a swab kit for collecting samples of cellular material from body cavities and storing the collected samples comprising:
 a sample collecting device as described above; and
 a sealable container adapted to receive and store at least a part of the sample collecting device.

Preferably the stick of the swab is breakable, such that only the swabbing tip and a small part of the stick have to be stored in the container, and preferably, the swab kit further comprising a liquid for protecting bacterial viability.

DETAILED DESCRIPTION OF THE INVENTION

Figure 1:
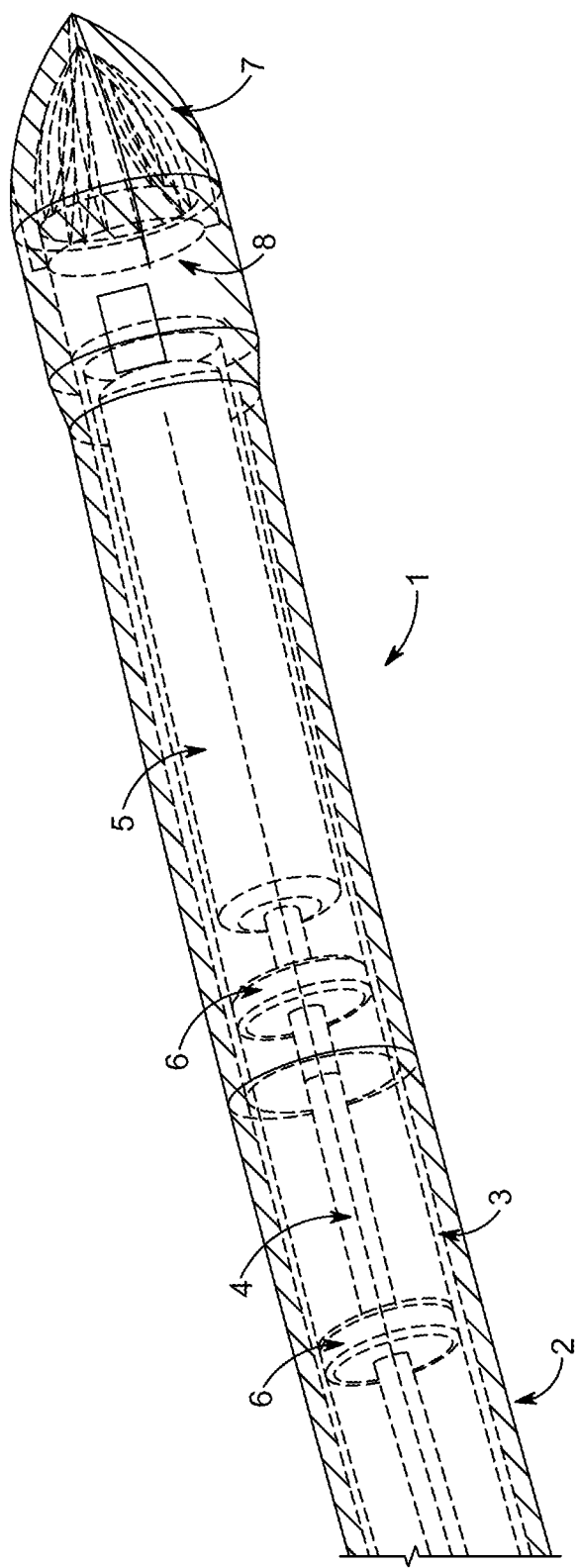
FIG. 1 shows a first embodiment of the presently disclosed sample collecting device.

The present disclosure relates to a sample collecting device for collecting samples of cellular material from body cavities comprising:
 an outer tubular member;
 an inner tubular member slidably arranged inside the outer tubular member;
 a swab comprising a stick; and a swabbing tip;
 one or more guiding elements configured to support and slidably arrange the swab in the inner tubular member such that there is a free space around the swabbing tip; and
 a flexible valve arranged at a distal end of the outer tubular member, the device configured such that:
 in a storage configuration, the valve is closed and seals the distal end of the outer tubular member, and
 in a sampling configuration, the valve is open in a position such that the swab can be slid in a longitudinal direction of the device to extend through the distal end of the outer tubular member without the swab being in contact with the valve.

Preferably, the sample collecting is a microbiological swab or a bacterial swab. The device is arranged such that there is a free space around the swabbing tip during insertion and retraction of the device through a possibly narrow passage. This arrangement prevents that the swabbing tip is contaminated. In order to achieve that the swabbing tip does not touch the inner tubular member, the outer diameter of the swabbing tip is smaller than the inner diameter of the inner tubular member, and the stick that holds the swabbing tip is guided inside the tubular member such that it does not touch the inner tubular member.

Preferably, the stick is breakable, which allows the swab to be stored in a smaller container after being used.

Valve and Arrangement of Distal End of the Device

As stated, the device has two configurations:
 In the storage configuration, the valve is closed and seals the distal end of the outer tubular member. Storage configuration refers to the swab being inserted, retracted or transported. In this configuration, the swab is preferably located inside the inner tubular member, which is located inside the outer tubular member. Preferably, the swabbing tip does not extend beyond the distal end of the outer tubular member in this configuration while the distal end is closed/sealed. The proximal end of the device is not necessarily closed/sealed.
 In the sampling configuration, the valve is open in a position such that the swab can be slid in a longitudinal direction of the device to extend through the distal end of the outer tubular member without the swab being in contact with the valve. The sampling configuration is typically used after the distal end of the device has been introduced to an area from which samples are to be collected.

Furthermore, in one embodiment, in the storage configuration, a distal end of the inner tubular member is arranged proximal to the distal end of the outer tubular member, and in the sampling configuration, the inner tubular member extends through the distal end of the outer tubular member, thereby holding the valve in the open position. This means that in the storage configuration, the distal end of the inner tubular member does not extend beyond the distal end of the outer tubular member. The inner tubular member is slidably arranged inside the outer tubular member. Thus, if the inner tubular is slid in the longitudinal direction of the device towards the distal end of the device, it will at a certain point extend beyond the distal end of the outer tubular member. An example of this scenario is shown in FIG. 3c. In the example, the inner tubular member maintains the valve in an open position such that the swabbing tip inside the tubular member will not be in contact with the valve if it is slid into the sampling configuration from this position.

The valve may take different shapes and properties. In one embodiment, the valve is an elastic component preventing backflow when the valve is closed in the storage configuration. The prevention of backflow prevents that the swabbing tip is contaminated during insertion and retraction of the device. Moreover, the valve may be arranged to close by flexing back when the inner tubular member is retracted from extending through the distal end of the outer tubular member in the sampling configuration, which protects the swabbing tip from being contaminated. One advantage of a valve that flexes back automatically when the inner tubular member is retracted is that the device may be operated only by pushing inner tubular member and swab in the longitudinal direction of the device towards the distal end; when the force is released, a mechanism may retract the inner tubular member automatically, and, as a consequence, the valve closes. One example of a valve that may be suitable for the the sample collecting device according to the present disclosure is a duckbill valve or a lip valve. A duckbill valve is valve, typically made of an elastomer, for preventing contamination due to backflow while allowing forward flow. Usually, duckbills are self-contained i.e. the sealing function is an integral part of a one-piece elastomeric component. A duckbill can be attached to e.g. pipes or tubes in different ways, for example by threading it around the tube as shown in FIGS. 3a-d. The valve may also be formed as an integral piece with the outer tubular member. The duckbill or lip valve may comprise one pair of lips forming a slit, or two pairs of lips forming two slits in a criss-cross orientation on the duckbill or lip valve (as shown in FIGS. 3a-d) or three or more pairs of lips, wherein the lips are closed in the storage configuration (FIG. 3a) and the lips are open in the sampling configuration (FIG. 3d).

In one embodiment, the flexible valve is arranged such that the swab cannot come in contact with an inner distal end of the flexible valve in the storage configuration. An inner distal end may be defined as the inside of the flexible valve at its distal, i.e. the end that may first come in contact with a contaminated area when inserted into for example a nose. Preferably, this is achieved without any additional elements or tubes between the flexible valve and the inner tubular member. In one embodiment the valve comprises at least one inner point at a distance removed from the distal end of the valve, wherein the inner point prevents the distal end of the swab and/or the inner tubular to be slid further towards the distal end of the valve in the storage configuration. An example of such an embodiment is shown in FIG. 3b. FIG. 3b shows a sample collecting device in a storage configuration. The inner point 11 (which is on the inside of the valve in relation to indicated point in the drawing) blocks the swab and the inner tubular member from reaching the distal end of the valve in this configuration. The distal end of the valve or any other part of the outside of the valve could come in contact with contaminated areas during insertion.

The sampling configuration of the same embodiment of the sample collecting device is shown in FIG. 3d. In this configuring, in order to avoid that the inner tubular member and/or the swab is contact with the outer tubular member, all parts of the valve distal to the at least one inner point (11) protrude radially outwardly in relation to the inner tubular member in the sampling configuration. It can be seen that the at least one inner point supports/holds the flexible valve in an open position. In this way it can be avoided that the swab and inner tubular member is in contact with any part of the outside of the valve and the edges of the opening of the valve. The parts of the valve that are positioned distal in relation to the inner point, in particular the edges of the opening of the valve, are not in contact with the inner tubular member and/or the swab since the flex radially outwardly from the inner point, which acts as a point of support. In one embodiment the valve and the inner tubular member are internally arranged such that the swab cannot come in contact with an inner distal end of the flexible valve.

In one embodiment the flexible valve is formed as a duckbill or lip valve. A sidewall of the flexible valve may be arranged such that the swab cannot come in contact with an inner distal end of the flexible valve in the storage configuration. In a duckbill/lip valve embodiment, the slits or lips may therefore extend from the distal end of the valve towards a proximal end of the valve inside the valve in the storage configuration, thereby preventing that the swab comes in contact with an inner distal end of the flexible valve.

As stated, in the sampling configuration the swab is slid in a longitudinal direction of the device towards the distal end to extend through the distal end without touching the valve, which is open in the sampling configuration. In one embodiment the inner tubular member maintains the valve in an open position in the sampling configuration, as shown in e.g. FIG. 3d. In this position, preferably the distal end of the inner tubular member is arranged distal to the valve (shown in e.g. FIG. 3d—the distal end of the inner tubular member extends beyond the distal end of the valve). In this position, there is no risk that the swabbing tip touches the valve, which may have been contaminated during insertion.

The device may be telescopic, wherein the telescopic device is collapsed in the storage configuration and extended in the sampling configuration. Telescopic in this context may refer to the outer tubular member, inner tubular member and swab being slidable in relation to each other, preferably in such a way that from the storage configuration (wherein the inner tubular member and the swab do not extend distally in relation to the distal end of the outer tubular member), the inner tubular is in a first step slid in relation to the outer tubular member, and in a second step the swab is slid in relation to the inner tubular member and the outer tubular member when preparing the device for collecting samples. In this regard, an intermediate configuration between the storage configuration and sampling configuration corresponds to the distal end of the inner tubular member being located distal to the distal end of the outer tubular member, but the swab stays inside the inner tubular member, as shown in FIG. 3c. In the sampling configuration, the inner tubular member may then extend through the distal end of the outer tubular member and the swab extend through the distal end of the inner tubular member, as shown in FIG. 3d. After having collected the samples, the configuration of the device is typically changed from sampling configuration to storage configuration before the device is retracted from the area where samples have been collected. Preferably, the swabbing tip is protected, i.e. not exposed, also when the device is removed from the area where samples are collected, e.g. when the device is retracted through the anterior nasal passage. The above steps are then preferably reversed such that the swab is first slid in relation to the inner tubular member, and the inner tubular member is then slid in relation to the outer tubular member.

Guiding Elements

The guiding elements support and slidably arrange the swab in the inner tubular member such that there is a free space around the swabbing tip. An example of guiding elements (6) is shown in FIG. 1. The outer diameter of the swabbing tip 5 is smaller than the inner diameter of the inner tubular member 3. As can be seen in the example of FIG. 1, the guiding elements 5 are mounted or attached to the stick 4. The guiding elements may be formed as an integral part of the stick. The guiding members on the stick preferably abut the inside of the inner tubular member. In FIG. 1 there is a small space between the swabbing tip and the inner tubular member. Since the inner tubular member is inside the outer tubular member, there is implicitly also a space between the swabbing tip and the outer tubular member. The guiding elements may be transversally extending elements attached to the stick and/or annular extensions/protrusions/rings on the stick as in the example of FIG. 1.

Alternatively the guiding elements may be part of the inner tubular member. In one embodiment the guiding elements are mounted on the inside of the inner tubular member. In this case, the guiding elements may be shaped as rings through which the stick is slid.

Locking Elements

In order to control the sliding movements of the inner tubular member and the swab in relation to each other and in relation to the outer tubular member, the sample collecting device of the present disclosure may comprise locking elements.

In one embodiment of the sample collecting device, the inner tubular member and the swab are configured to extend telescopically through the distal end of the outer tubular member when a force is asserted on a proximal end of the stick or inner tubular member in the longitudinal direction of the device towards the distal end of the device, such that > the inner tubular member moves in the longitudinal direction of the device in relation to the outer member in a first configuration, and
>
> the swab moves in the longitudinal direction of the inner tubular member and the inner tubular member is locked in relation to the outer tubular member in a second configuration.

Such a movement divided into two steps may be achieved by having one or more locking elements inside the tubes. For example, if the swab and the inner tubular member are locked in relation to each other by means of a first locking element in the first configuration, the inner tubular member and the outer tubular member will move in relation to each other when either one of the inner tubular member and the swab is pushed in the distal direction of the device. Such a locking mechanism may be achieved by e.g. a small transversal extension on the guiding elements on the stick that fits into a socket or recess in the inner tubular member. Other first locking elements are possible, which maintain the swab and inner tubular member in a fixed position in relation to each other in the first configuration. In one embodiment, the device comprises a first locking element for limiting the movement in the longitudinal direction of the device of the swab in relation to the inner tubular member.

As described above, in one embodiment of the sample collecting device, the inner tubular member and the swab are configured to extend telescopically through the distal end of the outer tubular member when a force is asserted on a proximal end of the stick or inner tubular member in the longitudinal direction of the device towards the distal end of the device. The device may be arranged such that in a sampling process the device starts in a storage configuration, then enters the sampling configuration in two steps as described. Preferably the device should be arranged such that an even force forward enables a substantially smooth two-step insertion of the swabbing tip. Similarly a pulling force backwards may retract the swab and inner tubular member back to the storage configuration after the sample has been collected. A spring or the like may also be used to move the device back to the storage configuration after a sample has been collected.

The device may also comprise a second locking element for limiting the movement in the longitudinal direction of the device of the inner tubular member in relation to the outer tubular member. Such a locking element may be any kind of element blocking further distal extension of the inner tubular member in relation the outer tubular member.

Preferably, the two locking elements are combined. The result of such a combination is that one pushing movement by the user may extend the device telescopically in two steps. In the first step, the inner tubular member is pushed to extend as shown in FIG. 3c, and in the second step the swab is released from its locked position and extends out of the inner tubular member.

The locking elements may also be used when changing the device from the device from the sampling configuration to the storing configuration. This means that, starting from the sampling configuration, if the swab is pulled in a longitudinal direction of the device toward the proximal end, the swab first moves in the longitudinal direction of the inner tubular member while the inner tubular member is locked in relation to the outer tubular. When the swab has reached a locking position in relation to the inner tubular member, the inner tubular member starts moving in relation to the outer tubular member if the pulling movement of the user towards the proximal end of the device is continued. In this way, one single pulling movement may retract the device from the sampling configuration to the storing configuration while the swabbing tip is not in direct contact with the valve.

Swabbing Tip

Preferably, the stick of the swab is breakable, which allows the swab to be stored in a smaller container after being used.

The swabbing tip is preferably securely attached to the distal end of the stick or an integral part of the stick and adapted to collect samples of cellular material. Preferably the tip is sterile and made of an absorbent and/or adhesive material. The swabbing tip may also be made of a porous material and the swabbing tip may be made of a material selected from the group of: cotton, wool, polyester, polyurethane foam or based on artificial fiber.

The swab may be a replaceable swab, preferably a disposable swab.

Sizes and Shapes

The presently disclosed sample collecting device may be slightly curved, which may further improve the device for some cases. Advantages related to a curved design is that in some anatomical contexts, it may be easier to introduce the device if is slightly curved. Furthermore, it may give the user better visibility of the actual sampling point i.e. the swabbing tip. In a slightly curved version of the device, the outer tubular member is preferably rigid, whereas the inner tubular member and swab are flexible in order to be able to slide inside the slightly curved tubular member. The combination of a rigid outer tubular member, a flexible inner tubular member and a flexible valve is suitable for providing a solution wherein the swabbing tip is not in contact with any contaminated area during insertion and at the same time can be inserted without the risk of bending, breaking or being deformed. In the curved version, the device is preferably curved between 0 and 20°, more preferably between 0 and 10°, most preferably between 0 and 7°.

The size of the device should be such that the device is suitable for being introduced in a narrow passage of the body e.g. through the anterior nasal passage. Therefore, the device preferably has the shape of a thin stick, possibly the size of a standard bacterial swab with two thin covers (tubular members) and a small space between the swabbing tip and the inner tubular member.

In one embodiment, the diameter of the outer tubular member (corresponding to the diameter of the device) is smaller than 8 mm, preferably smaller than 7 mm, even more preferably smaller than 6 mm, or smaller than 5 mm, or smaller than 4 mm, most preferably smaller than 3 mm.

The inner tubular member may be placed very close to the outer tubular member. The two tubular members may be in contact and slidably arranged to each other. There may also be a small gap between the outer tubular member and the inner tubular member. In one embodiment, the outer diameter of the inner tubular member is less than 0.5 mm, or less than 0.4 mm, or less than 0.3 mm, or less than 0.2 mm, or less than 0.1 mm smaller than the inner diameter of the outer tubular member.

The swab may be a standard bacterial swab. The stick or shaft of the swab is typically made of a plastic material, wood or metal, and relatively thin. In one embodiment, the diameter of the stick is smaller than 3 mm, more preferably smaller than 2 mm, most preferably smaller than 1 mm.

As stated, there should be a free space around the swabbing tip. Therefore, in one embodiment, the diameter of the swabbing tip is less than 6 mm, or less than 4 mm, or less than 3 mm, or less than 2 mm. The maximum diameter of the swabbing for an embodiment of the device depends on the inner diameter of the inner tubular member, and, implicitly on the diameter of the outer tubular member.

The suitable length of the device depends on the conditions and environment the device operates in. A shorter device is logically easier to transport and requires less space, but a longer device may be beneficial for some body cavities. An example of a relatively standard-sized cotton swab is 12 cm. The length of the presently disclosed sample collecting device may be less than 15 cm, or less than 12 cm, or less than 10 cm, or less than 8 cm. As described, the stick may also be breakable, which allows using a longer stick but only storing and transporting a shorter stick after use.

Cotton swabs that are commercially available come in a range of sizes. In one embodiment, the length of the swabbing tip is less than 20 mm, or less than 15 mm, or less than 10 mm, or less than 5 mm.

Swab Kit

The present disclosure further relates to a swab kit for collecting samples of cellular material from body cavities and storing the collected samples comprising:
   a sample collecting device as described above; and
   a sealable container adapted to receive and store at least a part of the sample collecting device.

Preferably, the sealable container comprises an elongate container for storing at least the swabbing tip and possibly at least a part of the stick, the container having a hollow space, and a lid.

The swab kit may further comprise a liquid for protecting bacterial viability or for preserving the sample. The container is preferably hermetically sealable.

DETAILED DESCRIPTION OF THE DRAWINGS

The invention will in the following be described in greater detail with reference to the accompanying drawings. The drawings are exemplary and are intended to illustrate some of the features of the presently disclosed sample collecting device for collecting samples of cellular material from body cavities, and are not to be construed as limiting to the presently disclosed invention.

FIG. 1 shows a first embodiment of the presently disclosed sample collecting device (1). The sample collecting device has an outer tubular member (2) and an inner tubular member (3). In this example, the inner tubular member (3) is located very close to the outer tubular member (2). The two tubular members are in contact and slidably arranged to each other. Inside the inner tubular member (3) there is a swab comprising a stick (4) and a swabbing tip (5). The swab has two guiding elements (6) to support and slidably arrange the swab in the inner tubular member (3) such that there is a free space around the swabbing tip (5). There is a small gap between the swabbing tip (5) and the inner tubular member (3). The inner tubular member has a distal end (8), in the figure marked as a circle. In this embodiment a valve (7) is integrated in the outer tubular member (2). The valve (7) is closed in FIG. 1, which corresponds to the storage configuration.

Figure 2:
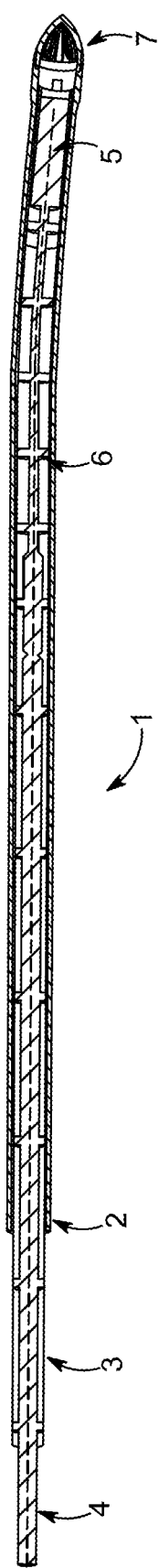
FIG. 2 shows a second embodiment of the presently disclosed sample collecting device.

FIG. 2 shows a second embodiment of the presently disclosed sample collecting device (1). The sample collecting device (1) has an outer tubular member (2) and an inner tubular member (3). It also has a swab comprising a stick (4) and a swabbing tip (5). In this embodiment, the guiding elements (6) are annular extensions on the stick (4). The length of these annular extension are shorter in the curved portion of the device (distal part of the device) and longer in the straight portion of the device (proximal part of the device). The valve (7) is closed in FIG. 2, corresponding to a storage configuration.

Figure 3A:
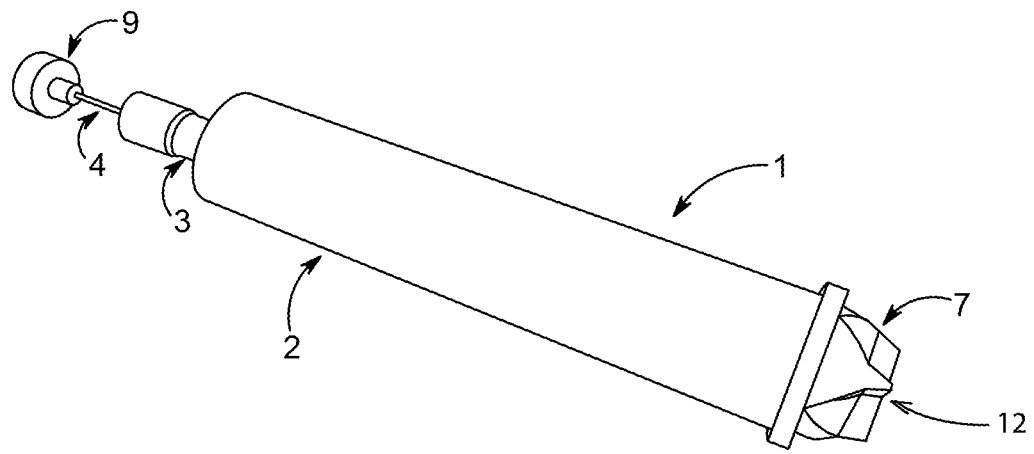
FIG. 3a shows a third embodiment of the presently disclosed sample collecting device in a storage configuration.
Figure 3B:
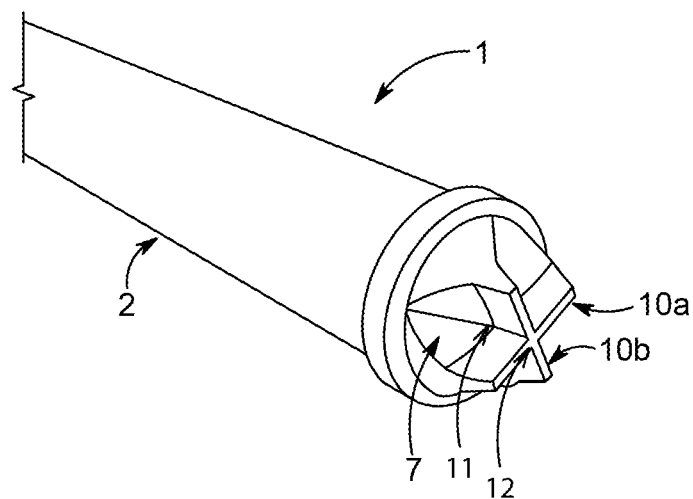
FIG. 3b shows the sample collecting device of FIG. 3a from a different angle.
Figure 3C:
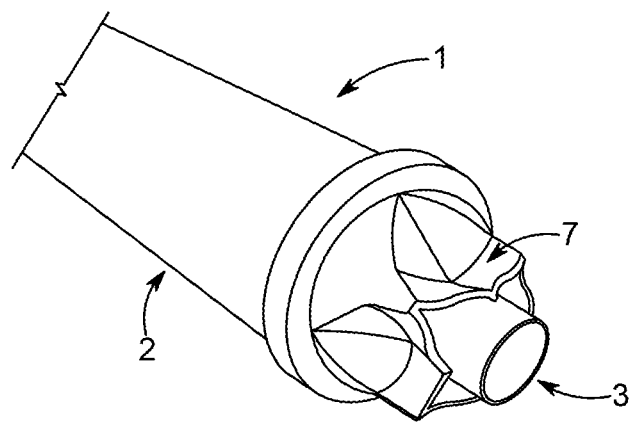
FIG. 3c shows the sample collecting device of FIGS. 3a and 3b, the inner tubular member extending beyond the distal end of the outer tubular member, holding the valve in the open position.
Figure 3D:
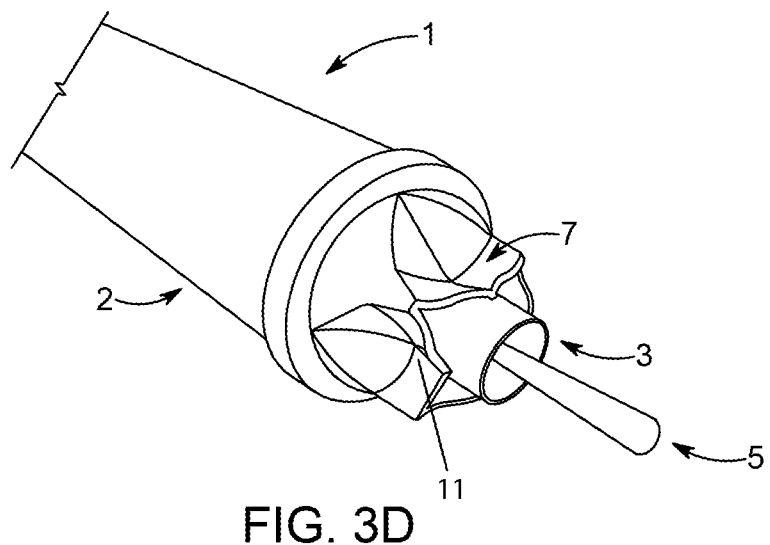
FIG. 3d shows the sample collecting device of FIGS. 3a, 3b and 3c in a sampling configuration.

FIG. 3a shows a third embodiment of the presently disclosed sample collecting device (1) in a storage configuration. The device (1) has an outer tubular member (2) and an inner tubular member (3). A stick (4) of the swab is visible, the stick (4) extending on the proximal side of the device (1). There is a pressure element (9) mounted on the proximal end of the stick (4), which can be used to push (or pull back) the swab in the device (1). In this embodiment, the valve (7) is a duckbill valve. In FIG. 3a, the duckbill valve is a a closed position.

FIG. 3b shows the sample collecting device (1) of FIG. 3a from a different angle. The duckbill valve (7) is still in a closed position, corresponding to a storage configuration. The duckbill valve (7) has two pairs of lips (10a and 10b) forming two slits in a criss-cross orientation on the duckbill valve (7).

In FIG. 3c, showing the sample collecting device (1) of FIGS. 3a and 3b in an intermediate configuration between a storage configuration and a sampling configuration, the inner tubular member (3) extends beyond the distal end of the outer tubular member (2). It also extends beyond the distal end of the valve (7), thereby holding the valve (7) in an open position. The swab (not shown) is inside the inner tubular member. The intermediate configuration is possible both when the device (1) goes from the storage configuration to the sampling configuration and when the device (1) goes from the sampling configuration to the storage configuration.

FIG. 3d shows the sample collecting device (1) of FIGS. 3a, 3b and 3c in a sampling configuration. In this configuration, the swabbing tip extends beyond both the distal end of the inner tubular member (3) and the valve (7). Since the inner tubular (3) in this configuration holds the valve (7) in an open position and extends beyond the distal end of the valve (7) there is no risk that the swabbing tip (5) is in contact with the valve (7) when the swab is slid in a longitudinal direction of the device from the storage configuration (in which the distal end of the swabbing tip (5) is located proximal to the valve (7)) to the sampling configuration shown in FIG. 3c.

Further Details of the Invention

1. A sample collecting device for collecting samples of cellular material from body cavities comprising:
   an outer tubular member;
   an inner tubular member slidably arranged inside the outer tubular member;
   a swab comprising a stick; and a swabbing tip;
   one or more guiding elements configured to support and slidably arrange the swab in the inner tubular member such that there is a free space around the swabbing tip; and a flexible valve arranged at a distal end of the outer tubular member, the device configured such that:
in a storage configuration, the valve is closed and seals the distal end of the outer tubular member, and
in a sampling configuration, the valve is open in a position such that the swab can be slid in a longitudinal direction of the device to extend through the distal end of the outer tubular member without the swab being in contact with the valve.

2. The sample collecting device according to any of the preceding items, wherein the device is a microbiological swab or a bacterial swab.

3. The sample collecting device according to any of the preceding items, wherein the sample collecting device is a nose swab sampling device.

4. The sample collecting device according to any of the preceding items, wherein the flexible valve is arranged such that the swab cannot come in contact with an inner distal end of the flexible valve in the storage configuration.

5. The sample collecting device according to any of the preceding items, wherein the valve comprises at least one inner point at a distance removed from the distal end of the valve, wherein the inner point prevents the distal end of the swab and/or the inner tubular to be slid further towards the distal end of the valve in the storage configuration.

6. The sample collecting device according to item 5, wherein all parts of the valve distal to the at least one inner point protrude radially outwardly in relation to the inner tubular member in the sampling configuration.

7. The sample collecting device according to any of items 5-6, wherein the valve is arranged such that no parts of the valve distal to the at least one inner point are in contact with the inner tube in the sampling configuration.

8. The sample collecting device according to any of items 5-7, wherein the at least one inner point holds the valve in the open position in the sampling configuration.

9. The sample collecting device according to any of the preceding items, wherein the valve and the inner tubular member are internally arranged such that the swab cannot come in contact with an inner distal end of the flexible valve.

10. The sample collecting device according to any of the preceding items, wherein
in the storage configuration, a distal end of the inner tubular member is arranged proximal to the distal end of the outer tubular member, and
in the sampling configuration, the inner tubular member extends through the distal end of the outer tubular member, thereby holding the valve in the open position.

11. The sample collecting device according to any of the preceding items, wherein the valve is an elastic component preventing backflow when the valve is closed in the storage configuration.

12. The sample collecting device according to item 11, wherein the valve is arranged to close by flexing back when the inner tubular member is retracted from extending through the distal end of the outer tubular member in the sampling configuration.

13. The sample collecting device according to any of the preceding items, wherein the valve is a duckbill valve or a lip valve.

14. The sample collecting device according to item 13, the duckbill or lip valve comprising one pair of lips forming a slit, or two pairs of lips forming two slits in a criss-cross orientation on the duckbill or lip valve, or three or more pairs of lips, wherein the lips are closed in the storage configuration and the lips are open in the sampling configuration.

15. The sample collecting device according to item 14, wherein, in the storage configuration, the slits or lips extend from the distal end of the valve towards a proximal end of the valve inside the valve, thereby preventing that the swab comes in contact with an inner distal end of the flexible valve.

16. The sample collecting device according to any of the preceding items, wherein a sidewall of the flexible valve is arranged such that the swab cannot come in contact with an inner distal end of the flexible valve in the storage configuration.

17. The sample collecting device according to any of the preceding items, wherein the distal end of the inner tubular member is arranged distal to the valve in the sampling configuration, thereby preventing contact between the swabbing tip and the valve.

18. The sample collecting device according to any of the preceding items, the device being telescopic, the telescopic device being collapsed in the storage configuration and extended in the sampling configuration.

19. The sample collecting device according to item 18, wherein, in the sampling configuration, the inner tubular member extends through the distal end of the outer tubular member and the swab extends through the distal end of the inner tubular member.

20. The sample collecting device according to any of the preceding items, wherein the guiding elements are transversally extending elements attached to the stick.

21. The sample collecting device according to any of the preceding items, wherein the guiding elements are annular extensions on the stick.

22. The sample collecting device according to any of the preceding items, wherein the guiding elements are mounted on the inside of the inner tubular member.

23. The sample collecting device according to any of the preceding items, wherein the inner tubular member and the swab are configured to extend telescopically through the distal end of the outer tubular member when a force is asserted on a proximal end of the stick or inner tubular member in the longitudinal direction of the device towards the distal end of the device, such that
the inner tubular member moves in the longitudinal direction of the device in relation to the outer member in a first configuration, and
the swab moves in the longitudinal direction of the inner tubular member and the inner tubular member is locked in relation to the outer tubular member in a second configuration.

24. The sample collecting device according to any of the preceding items, comprising a first locking element for limiting the movement in the longitudinal direction of the device of the swab in relation to the inner tubular member, and a second locking element for limiting the movement in the longitudinal direction of the device of the inner tubular member in relation to the outer tubular member.

25. The sample collecting device according to any of the preceding items, wherein the stick is breakable.

26. The sample collecting device according to any of the preceding items, wherein the swabbing tip is absorbent and/or adhesive.
27. The sample collecting device according to any of the preceding items, wherein the swabbing tip is made of a porous material.
28. The sample collecting device according to any of the preceding items, wherein the swabbing tip is made of cotton, wool, polyester, polyurethane foam or based on artificial fiber.
29. The sample collecting device according to any of the preceding items, wherein the outer tubular member is rigid, and the inner tubular member and swab are flexible.
30. The sample collecting device according to any of the preceding items, wherein the device is curved, preferably between 0 and 20°, more preferably between 0 and 10°, most preferably between 0 and 7°.
31. The sample collecting device according to any of the preceding items, wherein the diameter of the outer tubular member is smaller than 8 mm, or smaller than 7 mm, or smaller than 6 mm, or smaller than 5 mm, or smaller than 4 mm, or smaller than 3 mm.
32. The sample collecting device according to any of the preceding items, wherein the outer diameter of the inner tubular member is less than 0.5 mm, or less than 0.4 mm, or less than 0.3 mm, or less than 0.2 mm, or less than 0.1 mm smaller than the inner diameter of the outer tubular member.
33. The sample collecting device according to any of the preceding items, wherein the diameter of the stick is smaller than 3 mm, or smaller than 2 mm, or smaller than 1 mm.
34. The sample collecting device according to any of the preceding items, wherein the diameter of the swabbing tip is less than 6 mm, or less than 4 mm, or less than 3 mm, or less than 2 mm.
35. The sample collecting device according to any of the preceding items, wherein the length of the device is less than 15 cm, or less than 12 cm, or less than 10 cm, or less than 8 cm.
36. The sample collecting device according to any of the preceding items, wherein the length of the swabbing tip is less than 20 mm, or less than 15 mm, or less than 10 mm, or less than 5 mm.
37. The sample collecting device according to any of the preceding items, the outer tubular member further comprising a light channel extending along or inside the outer tubular member.
38. The sample collecting device according to any of the preceding items, further comprising a light source, preferably configured to emit light through the light channel.
39. The sample collecting device according to any of the preceding items, wherein the swab is replaceable, preferably a disposable swab.
40. A swab kit for collecting samples of cellular material from body cavities and storing the collected samples comprising:
    a sample collecting device according to any of the preceding items; and
    a sealable container adapted to receive and store at least a part of the sample collecting device.
41. The swab kit according to item 40, further comprising a liquid for protecting bacterial viability.

The invention claimed is:
1. A sample collecting device for collecting samples of cellular material from body cavities comprising:
    an outer tubular member;
    an inner tubular member slidably arranged inside the outer tubular member;
    a swab comprising a stick and a swabbing tip;
    one or more guiding elements configured to support and slidably arrange the swab in the inner tubular member such that there is a free space around the swabbing tip; and
    a flexible valve arranged at a distal end of the outer tubular member, the flexible valve having an opening with opening edges at a distal end of the flexible valve, the sample collecting device configured such that:
    in a storage configuration, the flexible valve is closed and seals the distal end of the outer tubular member, and in a sampling configuration, the flexible valve is open in a position such that the swab can be slid in a longitudinal direction of the sample collecting device to extend through the distal end of the outer tubular member without the swab being in contact with the flexible valve,
    wherein the flexible valve comprises at least one inner point at a distance removed from the distal end of the flexible valve, wherein the inner point prevents at least one of the swab and the inner tubular member from sliding further towards the distal end of the flexible valve in the storage configuration; and
    wherein the flexible valve is arranged such that no parts of the flexible valve distal to the at least one inner point are in contact with the inner tubular member in the sampling configuration;
    the flexible valve thereby being arranged such that the opening edges of the flexible valve cannot come into contact with the inner tubular member.
2. The sample collecting device according to claim 1, wherein the sample collecting device is a microbiological swab or a bacterial swab.
3. The sample collecting device according to claim 1, wherein the sample collecting device is a nose swab sampling device.
4. The sample collecting device according to claim 1, wherein the flexible valve is arranged such that the swab cannot come in contact with an inner distal end of the flexible valve in the storage configuration.
5. The sample collecting device according to claim 1, wherein all parts of the flexible valve distal to the at least one inner point protrude radially outwardly in relation to the inner tubular member in the sampling configuration.
6. The sample collecting device according to claim 1, wherein the at least one inner point holds the flexible valve in an open position in the sampling configuration.
7. The sample collecting device according to claim 1, wherein the flexible valve and the inner tubular member are internally arranged such that the swab cannot come in contact with an inner distal end of the flexible valve.
8. The sample collecting device according to claim 1, wherein
    in the storage configuration, a distal end of the inner tubular member is arranged proximal to the distal end of the outer tubular member, and
    in the sampling configuration, the inner tubular member extends through the distal end of the outer tubular member, thereby holding the flexible valve in the open position.

9. The sample collecting device according to claim 1, wherein the flexible valve is an elastic component preventing backflow when the flexible valve is closed in the storage configuration, and wherein the flexible valve is arranged to close by flexing back when the inner tubular member is retracted from extending through the distal end of the outer tubular member in the sampling configuration.

10. The sample collecting device according to claim 1, wherein the flexible valve is a duckbill valve or a lip valve, the duckbill valve or lip valve comprising one pair of lips forming a slit, or two pairs of lips forming two slits in a criss-cross orientation on the duckbill valve or lip valve, or three or more pairs of lips, wherein the lips are closed in the storage configuration and the lips are open in the sampling configuration.

11. The sample collecting device according to claim 1, wherein the distal end of the inner tubular member is arranged distal to the flexible valve in the sampling configuration, thereby preventing contact between the swabbing tip and the flexible valve.

12. The sample collecting device according to claim 11, wherein, in the storage configuration, the slits or lips extend from the distal end of the flexible valve towards a proximal end of the flexible valve inside the flexible valve, thereby preventing that the swab comes in contact with an inner distal end of the flexible valve.

13. The sample collecting device according to claim 1, wherein a sidewall of the flexible valve is arranged such that the swab cannot come in contact with an inner distal end of the flexible valve in the storage configuration.

14. The sample collecting device according to claim 1, the sample collecting device being a telescopic sample collecting device, the telescopic sample collecting device being collapsed in the storage configuration and extended in the sampling configuration, and wherein, in the sampling configuration, the inner tubular member extends through the distal end of the outer tubular member and the swab extends through the distal end of the inner tubular member.

15. The sample collecting device according to claim 1, wherein the guiding elements are transversally extending elements attached to the stick.

16. The sample collecting device according to claim 1, wherein the guiding elements are annular extensions on the stick.

17. The sample collecting device according to claim 1, comprising a first locking element for limiting movement of the swab in the longitudinal direction of the sample collecting device in relation to the inner tubular member, and a second locking element for limiting the movement in the longitudinal direction of the sample collecting device of the inner tubular member in relation to the outer tubular member.

18. The sample collecting device according to claim 1, wherein the swab is replaceable.

19. The sample collecting device according to claim 1, wherein the swab is a disposable swab.

20. A swab kit for collecting samples of cellular material from body cavities and storing the collected samples comprising:
   a sample collecting device for collecting samples of cellular material from body cavities comprising:
   an outer tubular member,
   an inner tubular member slidably arranged inside the outer tubular member,
   a swab comprising a stick and a swabbing tip,
   one or more guiding elements configured to support and slidably arrange the swab in the inner tubular member such that there is a free space around the swabbing tip, and
   a flexible valve arranged at a distal end of the outer tubular member, the flexible valve having an opening with opening edges at a distal end of the flexible valve,
   the sample collecting device configured such that:
   in a storage configuration, the flexible valve is closed and seals the distal end of the outer tubular member, and
   in a sampling configuration, the flexible valve is open in a position such that the swab can be slid in a longitudinal direction of the sample collecting device to extend through the distal end of the outer tubular member without the swab being in contact with the flexible valve,
   wherein the flexible valve comprises at least one inner point at a distance removed from the distal end of the flexible valve, wherein the inner point prevents at least one of the swab and the inner tubular member from sliding further towards the distal end of the flexible valve in the storage configuration, and
   wherein the flexible valve is arranged such that no parts of the flexible valve distal to the at least one inner point are in contact with the inner tubular member in the sampling configuration,
   the flexible valve thereby being arranged such that the opening edges of the flexible valve cannot come into contact with the inner tubular member; and
   a sealable container adapted to receive and store at least a part of the sample collecting device.

\* \* \* \* \*